US012675156B2

(12) United States Patent
     Cockram

(10) Patent No.:    US 12,675,156 B2
(45) Date of Patent:        Jul. 7, 2026

(54) EYE MONITORING SYSTEM AND METHOD

(71) Applicant: Sony Interactive Entertainment Inc.,
               Tokyo (JP)

(72) Inventor:  Philip Cockram, London (GB)

(73) Assignee: Sony Interactive Entertainment Inc.,
               Tokyo (JP)

( * ) Notice:   Subject to any disclaimer, the term of this
                patent is extended or adjusted under 35
                U.S.C. 154(b) by 343 days.

(21) Appl. No.: 18/353,944

(22) Filed:     Jul. 18, 2023

(65)                Prior Publication Data

US 2024/0028114 A1       Jan. 25, 2024

(30)        Foreign Application Priority Data

Jul. 21, 2022    (GB) ...................................... 2210659

(51) Int. Cl.
     *A61B 3/02*            (2006.01)
     *A61B 3/10*            (2006.01)
                    (Continued)
(52) U.S. Cl.
     CPC ..............  *G06F 3/013* (2013.01); *A61B 3/113*
          (2013.01); *A61B 5/01* (2013.01); *G01K 3/10*
                                              (2013.01);
                    (Continued)
(58) Field of Classification Search
     CPC ......... A61B 3/02; A61B 3/102; A61B 3/1025;
                   A61B 3/113; A61B 3/1015; A61B
                                           3/1225;
                    (Continued)

(56)                References Cited

U.S. PATENT DOCUMENTS 9,798,385 B1 *  10/2017  Das ........................ H04L 67/535
2009/0066722 A1 *   3/2009  Kriger ................... G09B 17/00
                                                           345/619
                    (Continued)

FOREIGN PATENT DOCUMENTS

CN        114859557 A      8/2022
EP          4310638 A1     1/2024
                    (Continued)

OTHER PUBLICATIONS

Search Report for corresponding GB Application No. 2210659.5, 5
pages, dated Jan. 23, 2023.
                    (Continued)

*Primary Examiner* — Dawayne Pinkney
(74) *Attorney, Agent, or Firm* — Fish & Richardson P.C.

(57)                  ABSTRACT

A system for use with a head-mountable display device,
HMD, operable to present content to a user, the system
comprising a temperature sensor unit configured to detect a
temperature associated with at least one of the user's eyes
and/or an ambient temperature associated with the HMD, a
blink sensor unit configured to detect blinking of one or both
of the user's eyes, a threshold determination unit configured
to determine a threshold value for a blink rate of the user in
dependence upon the one or more detected temperatures,
and a processing unit configured to determine a blink rate of
the user in dependence upon the detected blinks, and to
modify the content presented by the HMD in response to the
blink rate of the user falling below the threshold value.

20 Claims, 3 Drawing Sheets

(51) Int. Cl.

| | |
|---|---|
| *A61B 3/113* | (2006.01) |
| *A61B 5/01* | (2006.01) |
| *G01K 3/10* | (2006.01) |
| *G02B 27/00* | (2006.01) |
| *G02B 27/01* | (2006.01) |
| *G06F 3/01* | (2006.01) |

(52) U.S. Cl.
CPC ....... *G02B 27/0093* (2013.01); *G02B 27/017* (2013.01)

(58) Field of Classification Search
CPC .... A61B 3/024; G02B 27/01; G02B 27/0101; G02B 27/0149; G02B 23/00; G02B 27/0093; G02B 27/017; G02B 2027/014
USPC ................ 351/246, 200, 205–206, 209–210, 351/221–223; 359/630–633, 404, 407
See application file for complete search history.

(56) References Cited

U.S. PATENT DOCUMENTS

| | | | |
|---|---|---|---|
| 2017/0127055 | A1 | 5/2017 | Khabiri |
| 2018/0246568 | A1 | 8/2018 | Holz et al. |
| 2020/0359886 | A1 | 11/2020 | Azar |
| 2021/0134245 | A1* | 5/2021 | Bonnier ............... G06V 40/193 |
| 2021/0142765 | A1* | 5/2021 | Malhotra ................. G09G 5/10 |

FOREIGN PATENT DOCUMENTS

| | | | |
|---|---|---|---|
| WO | 9952479 | A1 | 10/1999 |
| WO | 2019046215 | A1 | 3/2019 |

OTHER PUBLICATIONS

Examination Report for corresponding GB Application No. 2210659.5, 5 pages, dated May 3, 2024.

* cited by examiner

Figure 5:
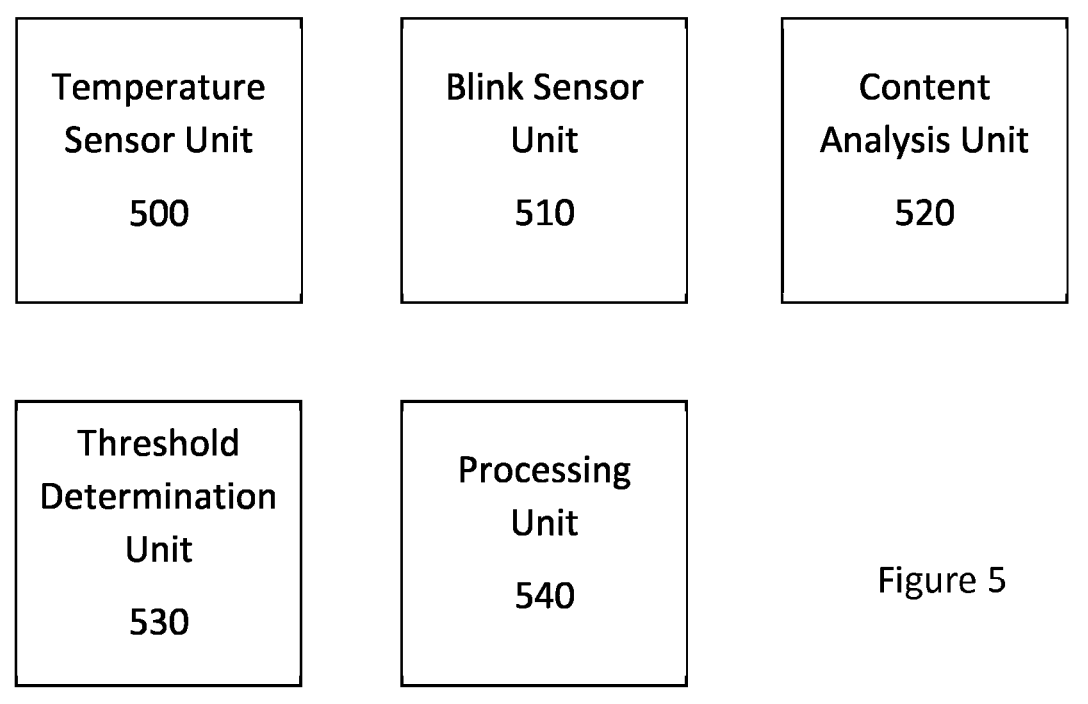

Temperature Sensor Unit

500

Blink Sensor Unit

510

Content Analysis Unit

520

Threshold Determination Unit

530

Processing Unit

EYE MONITORING SYSTEM AND METHOD

BACKGROUND OF THE INVENTION

Field of the Invention

This disclosure relates to an eye monitoring system and method.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The use of head-mountable display devices (HMDs) has become increasingly common in recent years, driven both by improvements to hardware and an increase in the number of applications for which an HMD is regarded as being suitable. For instance, hardware improvements have enabled a more portable approach to HMDs, along with improvements to the ability to generate immersive and engaging content. Further to this, the adaptation of devices such as mobile phones to provide an HMD experience (for instance, using a head-mountable mounting for a mobile phone) has increased the availability of HMD-based content for users.

In addition to the increasing adoption of these devices amongst the general public, for many users the duration for which these devices may be used has increased. This may be in part due to hardware improvements, such as increased battery life for wireless devices, or an increase in the range of content available to a user. For example, some HMD users may utilise an HMD for work (such as to reduce the need for a number of computer monitors on a desk, or to enable information to be presented in an overlaid fashion) or for extended gaming sessions.

Such an increase in use can lead to discomfort for a user, however. A first example of this is when using an HMD which has a poor weight distribution, as this can lead to a strain upon the user's neck or the like. Similarly, a user's eyes may also be impacted by extended use of an HMD; this can lead to eye strain, which can cause significant discomfort to the user which may last for a short period of time even after finishing using the HMD. It is therefore considered advantageous that the user experience for HMD users is improved so as to reduce a level of discomfort and/or to enable an increased use time before experiencing discomfort.

It is in the context of the above discussion that the present disclosure arises.

SUMMARY OF THE INVENTION

This disclosure is defined by claim 1.

Further respective aspects and features of the disclosure are defined in the appended claims.

It is to be understood that both the foregoing general description of the invention and the following detailed description are exemplary, but are not restrictive, of the invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5 schematically illustrates a content modification system.

DESCRIPTION OF THE EMBODIMENTS

Figures 1, 2:
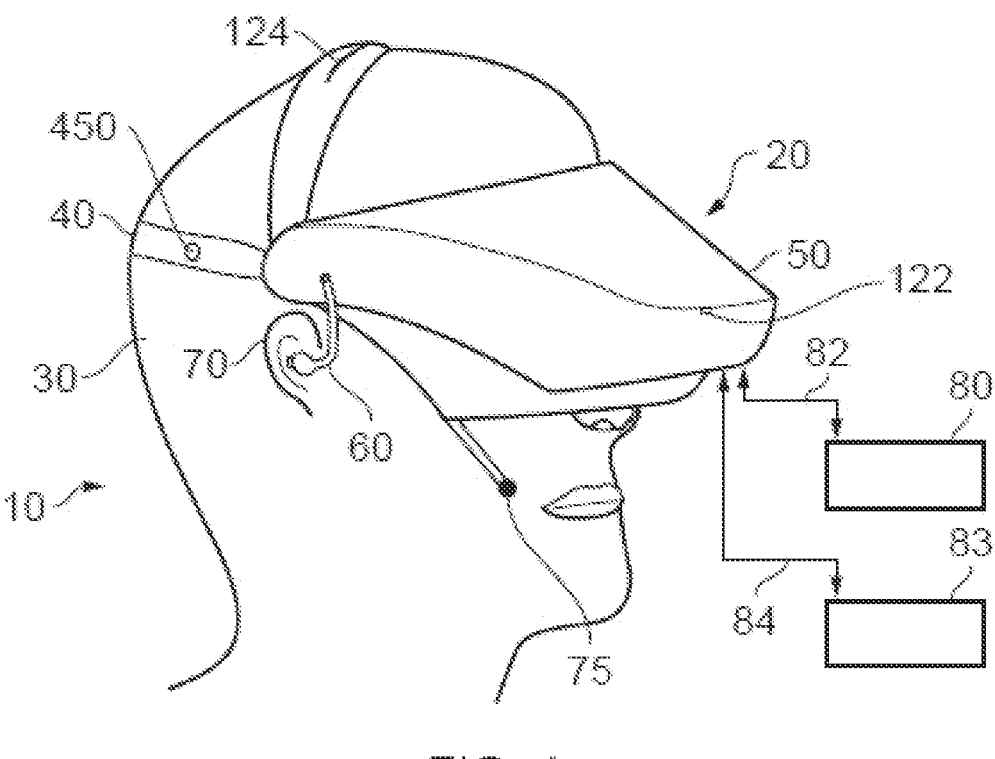
FIG. 1 schematically illustrates an HMD worn by a user.
FIG. 2 is a schematic plan view of an HMD.

Referring now to the drawings, wherein like reference numerals designate identical or corresponding parts throughout the several views, embodiments of the present disclosure are described.

Referring now to FIG. 1, a user 10 is wearing an HMD 20 (as an example of a generic head-mountable apparatus or virtual reality apparatus). The HMD comprises a frame 40, in this example formed of a rear strap and a top strap, and a display portion 50.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD.

The HMD has associated headphone audio transducers or earpieces 60 which fit into the user's left and right ears 70. The earpieces 60 replay an audio signal provided from an external source, which may be the same as the video signal source which provides the video signal for display to the user's eyes. A boom microphone 75 is mounted on the HMD so as to extend towards the user's mouth.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. A Bluetooth® antenna 124 may provide communication facilities or may simply be arranged as a directional antenna to allow a detection of the direction of a nearby Bluetooth transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection 82. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply 83 (including one or more batteries and/or being connectable to a mains power outlet) may be linked by a cable 84 to the HMD. Note that the power supply 83 and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the disclosure are applicable to an HMD having at least one electrical and/or optical cable linking the HMD to another device, such as a power supply and/or a video (and/or audio) signal source. So, embodiments of the disclosure can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply; or (d) an HMD having a wireless connection to a video and/or audio signal source and a cabled connection to a power supply.

If one or more cables are used, the physical position at which the cable 82 and/or 84 enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables 82, 84 relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160.

In embodiments of the present disclosure, it is considered that one or more additional elements may be provided as a part of an HMD. These may be provided in any suitable configuration within the HMD based upon the limitations of a particular device and the element so as to enable the functionality to be realised.

For example, one or more cameras may be provided within the HMD (or otherwise mounted upon it) to perform a gaze tracking function for one or both of the user's eyes. These one or more cameras may be operable to capture images of the user's eye or eyes for the purpose of identifying a gaze direction based upon a detected pupil location, for instance, and may be implemented in any suitable manner—for instance using visible or infra-red light, or using traditional or event camera based implementations.

These cameras may also be configured to be used as a part of a blink detection process for one or both of the user's eyes; for instance, images in which the user's pupils are not visible may be considered to correspond to a blink. Alternatively, or in addition, further imaging hardware and/or other sensors (such as sensors able to identify the activation of muscles associated with blinking) may be provided as a part of the HMD.

Alternatively, or in addition, one or more heat sensors may be provided which are operable to measure one or more temperatures associated with the HMD and its use. These temperatures may each be measured by the same sensor, or separate sensors may be provided which each record the temperatures of different aspects of the HMD and its use.

A first example of a sensor to perform a temperature detection is the use of one or more thermal cameras that are directed towards one or both of the user's eyes. Based upon the images captured by the one or more thermal cameras, the respective temperatures of one or more parts of the user's eye (or eyes) can be identified.

Alternatively, or in addition, an ambient temperature sensor may be provided which is operable to determine an air temperature within the HMD or otherwise proximate to the user's eyes (for instance, if the HMD does not have a well-defined volume such as in the case of a glasses-style augmented reality arrangement). This may be a sensor based upon measuring the changes in resistance for a thermally sensitive conductive element, for instance, or a sensor which uses thermocouples.

Figure 3:
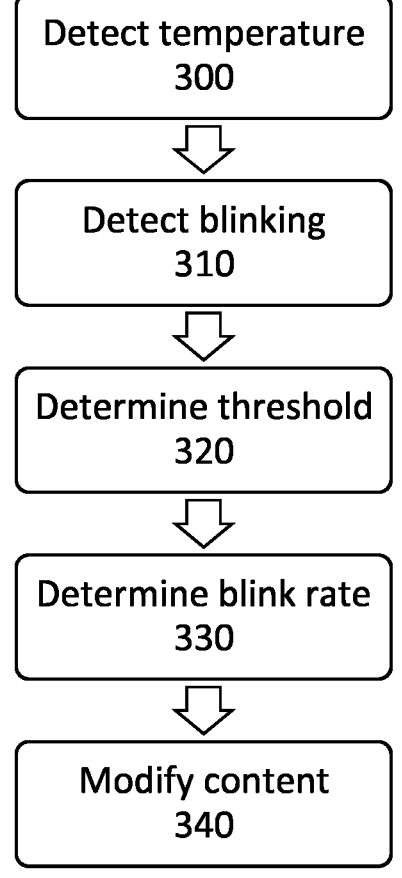
FIG. 3 schematically illustrates a content modification method.

FIG. 3 schematically illustrates a method for use with an HMD, operable to present content to a user, in which the operation of the HMD is modified in response to a blink rate of the user falling below a threshold value. The threshold value is determined in dependence upon at least one temperature measurement corresponding to the user's eyes or an ambient temperature associated with the HMD.

A step 300 comprises detecting a temperature associated with at least one of the user's eyes and/or an ambient temperature associated with the HMD. As described above, this may be implemented using any suitable temperature sensing element—for instance, a thermal camera imaging the user's eye, or a thermocouple-based detector for ambient temperature. In some cases, an indirect measurement may be made, such as measuring the temperature of the user's skin and using this to infer or estimate a temperature associated with at least one of the user's eyes and/or an ambient temperature associated with the HMD.

The ambient temperature may be the air temperature within an enclosed area defined by the HMD and the user's face, for example, or may be an air temperature in a location proximate to the user's eyes. Rather than being limited to a measure of the air temperature, the ambient temperature may be derived based upon the temperature of any element of the HMD. The ambient temperature is envisaged as being a measure by which the temperature conditions in which the user's eyes are present can be determined.

A step 310 comprises detecting blinking of one or both of the user's eyes. This may be performed using gaze tracking cameras, for instance, or may be performed by a dedicated sensor—such as a camera which is provided specifically for blink detection, or sensors which detect muscle motion or the like. A blink here refers to any event in which the user's eye (or eyes) rapidly close and open again. When only a single eye is subjected to blink detection, the difference between a blink and a wink (or a general closing of one or both of the eyes) may be determined in any suitable manner—for instance, based upon the duration of the action as a wink typically has a longer duration than a blink.

A step 320 comprises determining a threshold value for a blink rate of the user in dependence upon the one or more detected temperatures (that is, one or more of the ambient temperature detections and/or the eye temperature detections). The threshold value is determined such that the value is higher when the temperature is higher; that is, when it is warmer it is expected that the user is required to blink more frequently to maintain good eye health, as the rate at which the user's eyes will dry is proportional to the temperature. The threshold may be set by considering a probability that the user's eye is dry; this may be based upon a model of the human eye, the user's eye more specifically, or previous data collected from a number of users.

In some cases, a threshold may be selected from amongst a number of predetermined thresholds; alternatively, thresholds may be generated on the fly. In either case, the threshold determination may be based upon any suitable variables including temperature and user-specific quantities such as average blink rate when not using an HMD, and susceptibility to dry eyes. The threshold may also be varied in dependence upon the duration of use of the HMD in a given session, as the user may begin to experience discomfort based upon the duration in addition to that from dryness of the eyes. The threshold may be determined with any suitable frequency; for instance, every n minutes or seconds, in response to a change in the determined blink rate, and/or in response to a change in the detected temperature. These changes may be subject to a threshold difference being observed, so as to reduce the number of times the threshold is modified.

A step 330 comprises determining a blink rate of the user in dependence upon the detected blinks. This can be performed on a rolling average basis, for example, or in blocks of predetermined time periods (such as successively calculating a blink rate for thirty second periods throughout the use of the device); however, any suitable method for determining a rate of blinking for a user may be utilised as appropriate for a given implementation.

A step 340 comprises modifying the content presented by the HMD in response to the blink rate of the user falling below the threshold value. This modification of content can take any suitable form, with the intention of the modification being the reduction of discomfort experienced by the user. A first example of a modification is that of pausing the content; alternatively, or in addition, the user may be encouraged to remove the HMD temporarily. A second example is that of generating a visual or audio-based notification to the user to encourage blinking—this may be an explicit instruction, or may be content that is designed to induce a blink response from the user (such as a bright light or loud noise). Further features may also be provided to induce a blink, such as the generation of a puff of air towards the user's eyes; in some cases, the air that is used may be cooled so as to be below the ambient temperature and/or moistened so as to alleviate any dryness of the user's eyes.

Figure 4:
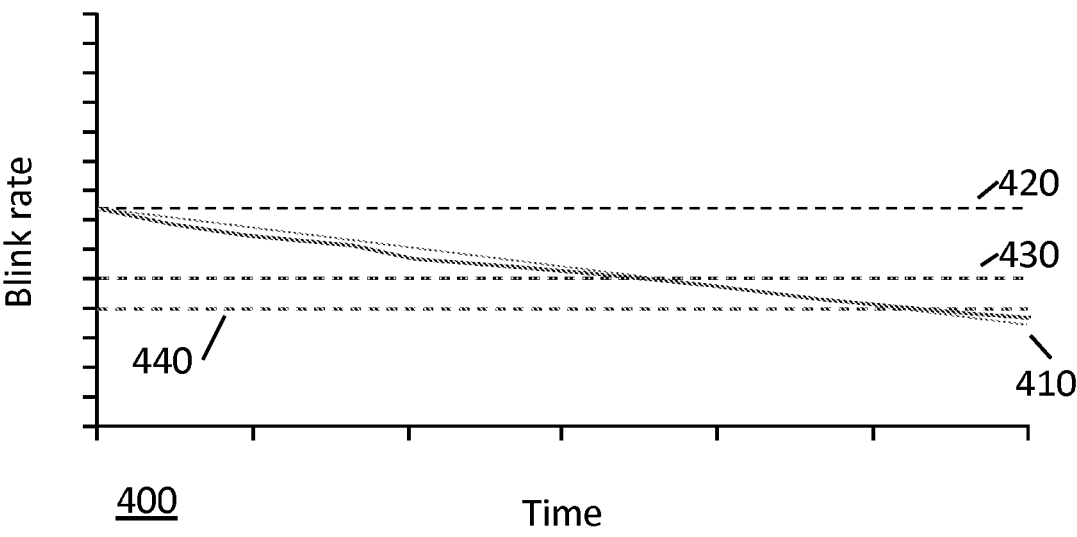
FIG. 4 schematically illustrates a graph of blink rate against time for an exemplary user.

FIG. 4 schematically illustrates an example of a blink rate of a typical user over time during use of an HMD. The graph 400 shows the blink rate 410 of the user decreasing over time, with a first line showing the blink rate and the second showing an average regression associated with this. A first dashed line 420 shows an average blink rate—this can be defined on a per-user basis or in a less specific manner so as to represent an average user or the average of a particular subset of users. The lines 430 and 440 respectively indicate threshold values if temperatures are high and if they are low; the line 430 is higher than the line 440 as (in line with the above discussion) the threshold is higher when the temperatures are higher.

Based upon the detected temperature, one of these thresholds may be selected, and at the point at which the line 410 crosses the selected threshold (430 or 440), the content modification according to step 340 of FIG. 3 is implemented.

It is considered that the discussion of the method according to FIG. 3 should not be regarded as being limiting upon the present disclosure; instead, a number of different modifications and variations to the described method are envisaged.

In some embodiments, it may be considered advantageous to calculate a rate of change of the blink rate of the user so as to generate a prediction of when the threshold will be exceeded. A similar calculation can be performed based upon changes in temperature. This can be advantageous in that user discomfort can be anticipated, and content modification can be performed in advance of the threshold being crossed (that is, the blink rate falls below the threshold value). This could be performed a predetermined amount of time before the threshold is predicted to be crossed, for example, or a predetermined percentage of the current usage session; similarly, a user profile may be used to specify a user preference for when the content modification should be performed.

In some embodiments, the modification to the content may comprise a modification to one or more display or rendering parameters so as to reduce the generation of heat in response to rising temperature. For instance, by reducing the image quality associated with displayed content processing units may be able to be operated at a lower capacity, thereby reducing the generated heat. Similarly, operating a display at a lower brightness and/or refresh rate can reduce the heat generated by a display panel. While this may result in a diminished user experience in respect of the appearance of the content, the duration of a user experience can be increased before user discomfort is experienced. In some cases, it may be considered that a user is able to provide information about a user's preferences in respect of this trade-off so as to ensure that the user's content experience is not rendered unsatisfactory.

In some embodiments, the content itself may also be monitored to determine an impact upon the user's eye health. In particular, it is noted that content with a high brightness and/or having mostly static image elements may have a higher impact upon the user's comfort levels when using an HMD. This can magnify the effects of increased temperature/reduced blinking, and therefore may be taken into account when determining a threshold value (such that a higher threshold value is specified when such content is being interacted with by a user). Alternatively, or in addition, a warning may be generated to the user indicating that the content has elements which may cause discomfort; this may encourage a user to change content, particularly if an alternative content is suggested which comprises fewer such elements.

FIG. 5 schematically illustrates a system for use with a head-mountable display device, HMD, operable to present content to a user, the system being operable to perform a content modification process. The system comprises a temperature sensor unit 500, a blink sensor unit 510, an optional content analysis unit 520, a threshold determination unit 530 and a processing unit 540. The functionality of these units may be distributed amongst any number of hardware elements, such as sensors, CPUs, and/or GPUs located at one or more devices.

In some embodiments, a significant portion of the processing may be performed using a processing unit (such as a CPU) located at the HMD; however, it is envisaged that some or all of the processing may instead be performed at an associated processing device (such as a games console) or a remote server in some embodiments. Similarly, while in many cases the sensors may be located at the HMD in other embodiments (particularly those in which a glasses-style see-through HMD is used) it may be appropriate to use sensors that are remote to the user in order to capture information—for instance, a thermal camera that is associated with a games console rather than the HMD.

The temperature sensor unit 500 is configured to detect a temperature associated with at least one of the user's eyes and/or an ambient temperature associated with the HMD. This unit comprises one or more detection elements, and optionally one or more processing elements that are configured to process the output of the detection elements. For instance, in some embodiments the temperature sensor unit 500 comprises a thermal camera configured to capture images of one or both of the user's eyes—an associated processing unit may process the captured images to determine a temperature associated with each of one or more portions of the user's eye and optionally compare this to a reference value.

The temperature sensor unit 500 may comprise any number of detection elements as appropriate to obtain the desired temperature readings; for instance, the temperature sensor unit 500 may comprise both a thermal camera and an ambient temperature sensing unit (such as a resistive thermal detection arrangement as discussed above) so as to obtain information about the temperature of the user's eye and the air surrounding the user's eyes.

In some embodiments, indirect detections of eye and/or ambient temperature may be made. For example, in some embodiments the temperature of a portion of the user's skin may be determined and this can be used to estimate the ambient and/or eye temperature accordingly. Similarly, a model may be used which estimates a temperature over time based upon one or more properties of the HMD (such as heat output by the HMD), the activity being engaged in by the user (such as whether they are engaging with content in a static or dynamic manner), and/or the user.

The blink sensor unit 510 is configured to detect blinking of one or both of the user's eyes. In some embodiments the blink sensor unit 510 may comprise a camera that is operable to detect a blink by one or both of the user's eyes; any type of imaging arrangement may be used to provide such a functionality. Alternatively, or in addition, one or more sensors may be provided which are able to detect blinks in a different manner; for instance, a sensor may be provided which is configured to detect muscle activation by a user from which a blink action can be derived.

In some embodiments, the blink sensor unit 510 is formed as a part of a gaze tracking arrangement associated with the HMD; that is to say that a gaze tracking unit arrangement may be configured to detect blinks in addition to a gaze direction, and this can be used in place of a dedicated sensor for detecting blinks.

The optional content analysis unit 520 is configured to determine one or more visual properties of the content. In particular, the content analysis unit 520 may be configured to identify an amount or proportion of static/dynamic elements on a display (for instance, based upon a number of elements and/or proportion of the display dedicated to each). Alternatively, or in addition, the content analysis unit 520 may be configured to determine a brightness associated with the content, or any other properties such as contrast, frame rate, and range of colours. These visual properties can be used as an indicator of how much discomfort a user may experience throughout use of the HMD due to the content itself.

The threshold determination unit 530 is configured to determine a threshold value for a blink rate of the user in dependence upon the one or more detected temperatures and, optionally, a current or average blink rate of the user. The determination by the threshold determination unit 530 may be performed in dependence upon a detected ambient temperature and/or eye temperature as appropriate for a given implementation. The threshold determination unit 530 may be configured to select from a plurality of predefined thresholds, or to calculate a new threshold value.

The threshold determination unit 530 may be configured to update the threshold value in response to a change in detected temperature, a change in detected blink rate, and/or an elapsed time—although any other schedule for updating the threshold value may also be considered appropriate in some embodiments. This can enable the threshold value to be adjusted dynamically throughout the usage of the HMD by the user.

In embodiments in which the optional content analysis unit 520 is provided, the threshold determination unit 530 may be configured to determine the threshold value in dependence upon the determined one or more visual properties of the content. For instance, if the content is determined to have a high brightness and/or a significant amount of static content then the threshold may be raised as to limit the chances of user discomfort.

The processing unit 540 is configured to determine a blink rate of the user in dependence upon the detected blinks, and to modify the content presented by the HMD in response to the blink rate of the user falling below the threshold value. This content modification may take any suitable form, with the intention of reducing user discomfort.

In some embodiments, the processing unit 540 is configured to generate a warning to be provided to the user when the blink rate of the user is determined to have fallen below the threshold value. This can enable a user to be informed as to the likelihood of discomfort (as users can often be unaware of the discomfort if they are immersed in content) and make a decision regarding this anticipated discomfort.

Alternatively, or in addition, the processing unit 540 may be configured to generate an instruction to the user to cause them to remove the HMD when the blink rate of the user is determined to have fallen below the threshold value. This can enable the ambient temperature to be reduced even if the user immediately returns the HMD to their head, due to the air flow that is introduced. The user may be instructed to take a break of a particular duration (such as a predetermined number of minutes, or a percentage of the time spent using the HMD, for example), which may be enforced by a timer associated with the content that prevents the user from continuing with the content for the determined amount of time.

Alternatively, or in addition, the processing unit 540 may be configured to generate a stimulus to induce one or more blinks from the user in dependence upon the blink rate of the user and/or a difference between the blink rate of the user and the threshold value. As described above, this may include any modification to the content as appropriate—including modifying one or more rendering and/or display parameters associated with the content in dependence upon a difference between the blink rate of the user and the threshold value. This can increase the blink rate of the user, particularly if performed frequently, thereby reducing the likelihood of user discomfort.

In some embodiments, the processing unit 540 is configured to determine a rate of change of blink rate of the user, to generate a prediction of when the blink rate of the user will fall below the threshold, and to modify the content in dependence upon this prediction. This can enable the content to be modified in advance of the user experiencing discomfort, or at least reducing the amount of discomfort that is experienced. One example of this is to display a warning to a user to indicate that they should have a break in their gameplay session in the next n minutes (n being any number), which may encourage a user to take a break as it can give them adequate warning to reach a good place to pause or save within a game (for example).

In some embodiments, the processing unit 540 may be configured to determine a rate of change of one or more of the detected temperatures; in such embodiments, the threshold determination unit 530 may be configured to estimate a future threshold value in dependence upon the determined rate of change of one or more of the detected temperatures. This may be advantageous in that a more accurate determination of when the blink rate will fall below the threshold value can be made, or in that it can be determined how quickly the user's comfort level will deteriorate due to changing temperatures. This information can be used to generate more effective and/or informative content modifications by the processing unit 540.

The arrangement of FIG. 5 is an example of a processor (for example, a GPU and/or CPU located in a games console or any other computing device) and sensing arrangement that is operable to modify content for display to a user, and in particular is operable to: detect a temperature associated with at least one of the user's eyes and/or an ambient temperature associated with the HMD; detect blinking of one or both of the user's eyes; optionally, determine one or more visual properties of the content; determine a threshold value for a blink rate of the user in dependence upon the one or more detected temperatures; and determine a blink rate of the user in dependence upon the detected blinks, and to modify the content presented by the HMD in response to the blink rate of the user falling below the threshold value.

The techniques described above may be implemented in hardware, software or combinations of the two. In the case that a software-controlled data processing apparatus is employed to implement one or more features of the embodiments, it will be appreciated that such software, and a storage or transmission medium such as a non-transitory machine-readable storage medium by which such software is provided, are also considered as embodiments of the disclosure.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

Embodiments of the present disclosure may be implemented in accordance with any one or more of the following numbered clauses:

1. A system for use with a head-mountable display device, HMD, operable to present content to a user, the system comprising: a temperature sensor unit configured to detect a temperature associated with at least one of the user's eyes and/or an ambient temperature associated with the HMD; a blink sensor unit configured to detect blinking of one or both of the user's eyes; a threshold determination unit configured to determine a threshold value for a blink rate of the user in dependence upon the one or more detected temperatures; and a processing unit configured to determine a blink rate of the user in dependence upon the detected blinks, and to modify the content presented by the HMD in response to the result of a comparison between the blink rate of the user and the threshold value.

2. A system according to clause 1, wherein the temperature sensor unit comprises a thermal camera configured to capture images of one or both of the user's eyes.

3. A system according to any preceding clause, wherein the blink sensor unit is formed as a part of a gaze tracking arrangement associated with the HMD.

4. A system according to any preceding clause, wherein the threshold determination unit is configured to update the threshold value in response to a change in detected temperature, a change in detected blink rate, and/or an elapsed time.

5. A system according to any preceding clause, wherein the threshold determination unit is configured to select from a plurality of predefined thresholds, or to calculate a new threshold value.

6. A system according to any preceding clause, wherein the processing unit is configured to determine a rate of change of blink rate of the user, to generate a prediction of when the blink rate of the user will fall below the threshold, and to modify the content in dependence upon this prediction.

7. A system according to any preceding clause, wherein the processing unit is configured to generate a warning to be provided to the user when the blink rate of the user is determined to have fallen below the threshold value.

8. A system according to any preceding clause, wherein the processing unit is configured to modify the content in dependence upon the magnitude of the difference between the blink rate of the user and the threshold value.

9. A system according to any preceding clause, wherein the processing unit is configured to generate a stimulus to induce one or more blinks from the user in dependence upon the blink rate of the user and/or a difference between the blink rate of the user and the threshold value.

10. A system according to any preceding clause, wherein the processing unit is configured to determine a rate of change of one or more of the detected temperatures, and wherein the threshold determination unit is configured to estimate a future threshold value in dependence upon the determined rate of change of one or more of the detected temperatures.

11. A system according to any preceding clause, wherein the processing unit is configured to modify one or more rendering and/or display parameters associated with the content in dependence upon a difference between the blink rate of the user and the threshold value.

12. A system according to any preceding clause, comprising a content analysis unit configured to determine one or more visual properties of the content, wherein the threshold determination unit is configured to determine the threshold value in dependence upon the determined one or more visual properties of the content.

13. A method for use with a head-mountable display device, HMD, operable to present content to a user, method comprising: detecting a temperature associated with at least one of the user's eyes and/or an ambient temperature associated with the HMD; detecting blinking of one or both of the user's eyes; determining a threshold value for a blink rate of the user in dependence upon the one or more detected temperatures; determining a blink rate of the user in dependence upon the detected blinks; and modifying the content presented by the HMD in response to the result of a comparison of the blink rate of the user and the threshold value.

14. Computer software which, when executed by a computer, causes the computer to carry out the method of clause 13.

15. A non-transitory machine-readable storage medium which stores computer software according to clause 14.

The invention claimed is:

1. A computer-implemented method comprising:

detecting (i) a temperature associated with one or both eyes of a user, or (ii) an ambient temperature associated with a head-mounted display (HMD);

determining a temperature-dependent threshold value for a blink rate of the user based at least on (i) the temperature associated with the one or both eyes of the user or (ii) the ambient temperature associated with the HMD;

detecting blinks of the one or both eyes of the user;

determining the blink rate associated with the blinks of the one or both eyes of the user;

determining that the blink rate satisfies the temperature-dependent threshold value; and modifying content presented on the HMD in response to determining that the blink rate satisfies the temperature-dependent threshold value.

2. The method of claim 1, wherein detecting the temperature associated with the one or both eyes of the user comprises detecting the temperature using a thermal camera configured to capture images of the one or both eyes of the user.

3. The method of claim 1, wherein detecting the ambient temperature associated with the HMD comprises detecting an air temperature within the HMD or an air temperature proximate to the one or both eyes of the user.

4. The method of claim 1, further comprising updating the temperature-dependent threshold value in response to a change in the detected temperature, a change in the determined blink rate, and/or an elapsed time.

5. The method of claim 1, wherein determining the temperature-dependent threshold value comprises selecting the temperature-dependent threshold value from a plurality of predefined temperature-dependent threshold values, or to calculate a new temperature-dependent threshold value.

6. The method of claim 1, wherein determining that the blink rate satisfies the temperature-dependent threshold value further comprises:

determining a rate of change of the blink rate; and predicting a time when the blink rate will fall below the temperature-dependent threshold value;

determining that the blink rate satisfies the temperature-dependent threshold value based on the prediction.

7. The method of claim 1, further comprising providing, to the user, a warning indicating that the content has elements causing discomfort to the one or both eyes, based on determining that the blink rate satisfies the temperature-dependent threshold value.

8. The method of claim 1, wherein modifying the content presented on the HMD comprises modifying the content based on a magnitude of a difference between the blink rate of the user and the temperature-dependent threshold value.

9. The method of claim 1, wherein modifying the content presented on the HMD comprises modifying one or more rendering and/or display parameters associated with the content based on a difference between the blink rate and the temperature-dependent threshold value.

10. The method of claim 1, wherein determining the temperature-dependent threshold value comprises:

determining a rate of a change of the detected temperature; and estimating the temperature-dependent threshold value based on the determined rate of the change of the detected temperature.

11. The method of claim 1, wherein determining the temperature-dependent threshold value comprises:

determining one or more visual properties of the content; and determining the temperature-dependent threshold value based on the determined one or more visual properties of the content.

12. The method of claim 1, wherein modifying the content presented on the HMD comprises pausing the content.

13. The method of claim 1, wherein modifying the content presented on the HMD comprises generating a visual notification and/or audio-based notification to the user to encourage the blinks.

14. The method of claim 1, wherein modifying the content presented on the HMD comprises generating air towards the one or both eyes of the user.

15. The method of claim 14, further comprising cooling and/or moistening the air.

16. A system comprising one or more computers and one or more storage devices storing instructions that are operable, when executed by the one or more computers to cause the one or more computers to perform operations comprising:

detecting (i) a temperature associated with one or both eyes of a user, or (ii) an ambient temperature associated with a head-mounted display (HMD);

determining a temperature-dependent threshold value for a blink rate of the user based at least on (i) the temperature associated with the one or both eyes of the user or (ii) the ambient temperature associated with the HMD;

detecting blinks of the one or both eyes of the user;

determining the blink rate associated with the blinks of the one or both eyes of the user;

determining that the blink rate satisfies the temperature-dependent threshold value; and modifying content presented on the HMD in response to determining that the blink rate satisfies the temperature-dependent threshold value.

17. The system of claim 16, the operations further comprising updating the temperature-dependent threshold value in response to a change in the detected temperature, a change in the determined blink rate, and/or an elapsed time.

18. The system of claim 16, wherein modifying the content presented on the HMD comprises generating a visual notification and/or audio-based notification to the user to encourage the blinks.

14

19. The system of claim 16, wherein modifying the content presented on the HMD comprises generating air towards the one or both eyes of the user.

20. One or more non-transitory computer storage media encoded with computer program instructions that when executed by one or more computers cause the one or more computers to perform operations comprising:

detecting (i) a temperature associated with one or both eyes of a user, or (ii) an ambient temperature associated with a head-mounted display (HMD);

determining a temperature-dependent threshold value for a blink rate of the user based at least on (i) the temperature associated with the one or both eyes of the user or (ii) the ambient temperature associated with the HMD;

detecting blinks of the one or both eyes of the user;

determining the blink rate associated with the blinks of the one or both eyes of the user;

determining that the blink rate satisfies the temperature-dependent threshold value; and modifying content presented on the HMD in response to determining that the blink rate satisfies the temperature-dependent threshold value.

* * * * *